United States Patent [19]

Kyriacou

[11] Patent Number: 5,183,569
[45] Date of Patent: Feb. 2, 1993

[54] FILTRATION APPARATUS AND PROCESS

[75] Inventor: Andreas Kyriacou, Toronto, Canada

[73] Assignee: Paradigm Biotechnologies Partnership, Toronto, Canada

[21] Appl. No.: 808,442

[22] Filed: Dec. 16, 1991

[51] Int. Cl.⁵ .......................................... B01D 61/20
[52] U.S. Cl. .................................. 210/636; 210/651; 210/247
[58] Field of Search ............ 210/247, 436, 472, 321.6, 210/321.66, 195.2, 196, 651, 636; 55/189

[56] References Cited

U.S. PATENT DOCUMENTS

| | | | |
|---|---|---|---|
| 2,696,818 | 12/1954 | Vah Loghem | 210/247 X |
| 3,630,378 | 12/1971 | Bauman . | |
| 3,705,100 | 12/1972 | Blatt et al. | 210/23 |
| 4,212,742 | 7/1980 | Solomon et al. | 210/247 |
| 4,276,176 | 6/1981 | Shorr | 210/651 X |
| 4,631,130 | 12/1986 | Watanabe | 210/651 |
| 4,753,733 | 6/1988 | Ramstack | 210/636 |
| 5,015,388 | 5/1991 | Pusineri et al. | 210/641 |

FOREIGN PATENT DOCUMENTS 160 of 1854 United Kingdom .

Primary Examiner—Frank Spear
Attorney, Agent, or Firm—Timothy R. Kroboth

[57] ABSTRACT

An improved filtration apparatus useful in particular for sampling a bulk, fluid, is provided. Advantageously, the filtration apparatus provides an air gap between a filtrate and the filtration medium. As a result, a bulk fluid is protected against potential contamination from the filtrate side of the filtration medium. Also provided is a technique for reducing filtration medium fouling, and for filtrate collection upon demand. Apparatus in accordance with the present invention, is useful, for example, in conjunction with monitoring urea concentration during dialysis.

11 Claims, 3 Drawing Sheets

FILTRATION APPARATUS AND PROCESS

BACKGROUND OF THE INVENTION

This invention relates generally to fluid filtration, in particular to collection of a filtrate from a bulk fluid being sampled, and especially to sampling of a body fluid for biomedical analysis or to fermentate sampling.

U.S. Pat. Nos. 5,015,388 to Pusineri et al, 4,753,733 to Ramstack, 4,631,130 to Watanabe, 4,212,742 to Solomon et al, and 3,705,100 to Blatt et al illustrate prior art, filtration techniques. In apparatus of the Pusineri et al, Solomon et al, and Blatt et al patents, a bulk fluid is passed over a fluid side surface of a filtration medium; fluid which does not pass through the filtration medium is collected from the bulk fluid or upstream side; crossflow filtration occurs; and filtrate is collected from the filtrate or downstream side of the filtration medium. The Ramstack process is directed to clearing membrane fouling.

A problem in filtration sampling can be backflow-caused contact between a filtrate and the filtration medium, with there being a potential for contamination of a bulk fluid being sampled, by any contaminants on the filtrate side of the filtration medium. Any contamination of a bulk fluid could have serious negative consequences. A further problem is filtration medium fouling. Also, in certain circumstances such as on-line biomedical sampling, air entrapment on the bulk fluid side of a filtration medium should be particularly avoided.

Accordingly, there is a need for an improved filtration apparatus, and in particular for an improved filtration apparatus useful for the collection of a filtrate from a bulk fluid being sampled. Beneficially, bulk fluid contamination would be prevented. Moreover, filtrate collection and thus bulk fluid sampling, upon demand, would be advantageously provided for. Furthermore, filtration medium fouling would be reduced. Such apparatus would be especially beneficial for certain on-line biomedical sampling if air entrapment on the bulk fluid side of a filtration medium could be avoided.

SUMMARY OF THE INVENTION

It is accordingly an object of the present invention to provide an improved filtration apparatus.

It is a further object for such apparatus to provide a filtrate sample in an on-line analysis of a bulk fluid.

It is a still further object to provide for such sampling upon demand.

It is an even further object to prevent contamination of a bulk fluid.

It is an additional object to reduce filtration medium fouling.

It is an even additional object to remove air from the bulk fluid side of a filtration apparatus during priming.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, an improved filtration apparatus in accordance with the present invention is provided. An important feature of the improved filtration apparatus is that it provides an air gap between a filtrate and the filtration medium. As a result, bulk fluid contamination by any contaminants on the filtrate side of the filtration medium, may be prevented.

The means for providing the air gap beneficially include a chamber in fluid communication with the filtration medium via a drip-forming channel. Advantageously, the chamber has a mouth of greater cross-section than a cross-section of the drip-forming channel, and has a filtrate exit of smaller cross-section than the mouth.

Also provided are novel filtration processes. In one such process, a fluid to be filtered, is passed into a filtration apparatus containing a filtration medium. The fluid beneficially enters the filtration apparatus from a direction countercurrent to filtrate flow through the filtration medium. Without having contacted a downstream surface of the filtration medium, the fluid is thereafter passed over an upstream side of the filtration medium to effect filtration. Filtrate is collected from the downstream side of the filtration medium, and contamination of fluid on the upstream side by any contaminants on the downstream side, may be prevented by forming an air gap between the filtrate and the filtration medium.

In another such process, a fluid to be filtered, is passed over an upstream side of a filtration medium, filtrate is collected from the downstream side of the filtration medium, and a closed loop is formed on the downstream side, as a result of which the filtration ceases and the only net force acting on the upstream side is exerted in the direction of fluid flow. Thereafter, the closed loop is opened to remove filtrate, as a result of which the filtration resumes and fresh filtrate may be collected upon demand.

In the drawing and in the detailed description of the invention that follows, there are shown and essentially described only preferred embodiments of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention, and which depicts preferred embodiments of an improved filtration apparatus and process in accordance with the present invention.

DETAILED DESCRIPTION OF THE INVENTION

The present invention is useful for the filtration of a liquid, and is particularly useful for the collection of a filtrate sample from a bulk fluid with return of the bulk fluid to its source, in an on-line analysis of the bulk fluid.

The fluid will typically be a particulate suspension or a solution of varying molecular weight solutes, or could be a mixture of such a suspension or solution. Accordingly, the present invention can be used for on-line sampling of a patient's blood during dialysis, and of broths from microbial and cell culture fermentations.

As will become understood, the present invention prevents backflow-caused contact between a filtrate and the filtration medium, and minimizes any possibility of contamination of a bulk fluid being sampled, by any contaminants such as chemicals and microbes, on the filtrate side of the filtration medium. Moreover, the present invention reduces filtration medium fouling, and provides for filtrate collection upon demand.

Figure 1:
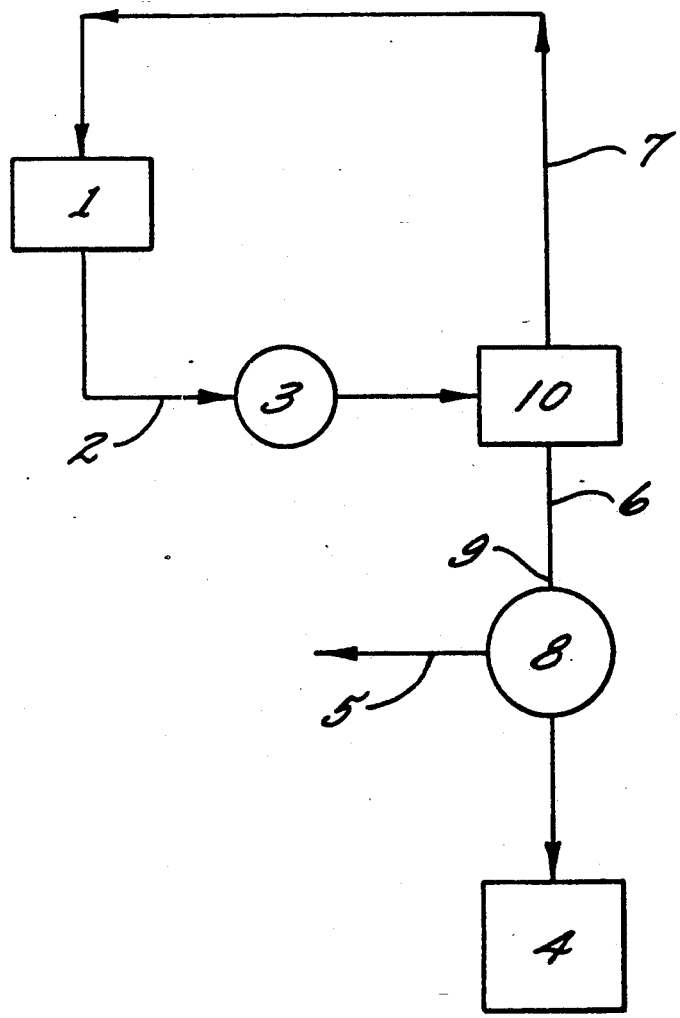
FIG. 1 is a block diagram depicting a preferred filtration apparatus in accordance with the present invention, in an on-line sampling of a bulk fluid.

Referring to FIG. 1, a preferred filtration apparatus 10 in accordance with the present invention, which is advantageously sterilizable, is represented in a block diagram depicting an application of the filtration apparatus in an on-line analysis of a bulk fluid. As schematically illustrated therein, a bulk fluid source 1 is in fluid communication with the filtration apparatus 10 via a tubular conduit 2. Conveniently, a conventional in-line pump 3 provides a suitable flow pressure for delivering the bulk fluid to the filtration apparatus. Filtrate is passed from the filtration apparatus to an analytical apparatus or device 4 or to a waste line 5 via a tubular conduit 6. Fluid which does not pass through the filtration medium of the filtration apparatus, is returned to source 1 via a line 7. As can be readily understood, in this way, a patient's blood may be sampled and analyzed during dialysis, or some other bulk fluid such as a fermentate may be sampled and the filtrate analyzed.

Figure 2:
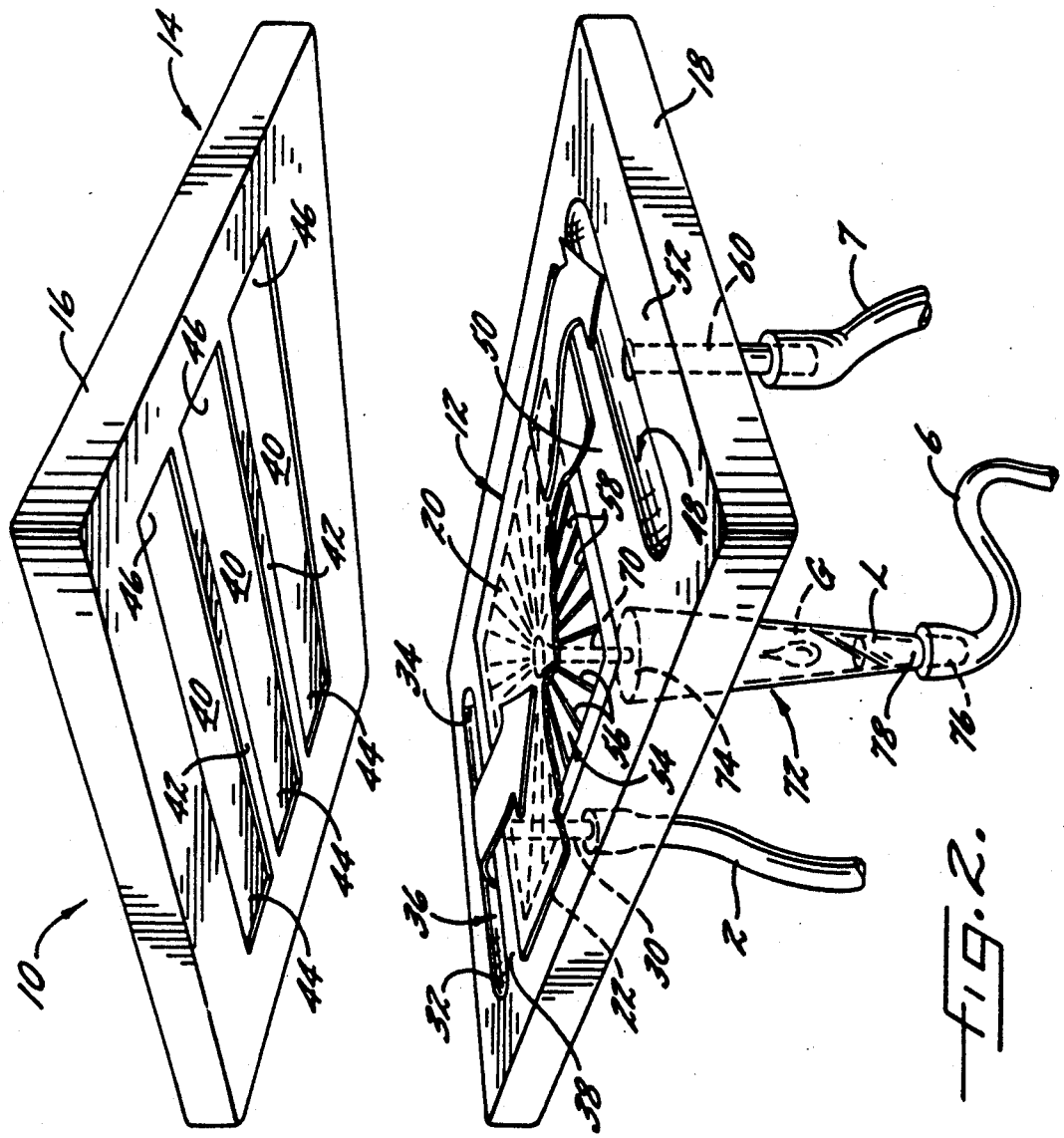
FIG. 2 is an exploded view of one embodiment of the filtration apparatus depicted in FIG. 1.

With reference now to FIG. 2, filtration apparatus 10 includes a filtration medium 12 disposed within a housing 14, conveniently formed by an upper or first member 16 and a lower or second member 18. The filtration medium may be planar, as depicted, or tubular as when, for instance, provided by a hollow tubular membrane, and may comprise one or an assembly of filtration members.

The size of the molecules retained by the filtration medium is a function of pore size and to some extent the chemistry of the filtration medium. Accordingly, the filtration medium is selected depending upon the fluid to be filtered and the filtrate to be collected, and may be a conventional filtration, ultrafiltration or microfiltration membrane. In the case of blood filtration, in particular plasmapheresis, a filtration membrane having a microporous structure with suitable cell-retaining pores, would be chosen.

Conventional configurations for housing 14 which provide for fluid flow over a fluid side or upstream surface 20 of the filtration medium, and filtrate collection from a filtrate side or downstream surface 22 of the filtration medium, could be used. However, as will become understood, a configuration in accordance with the present invention and particularly suitable for use in bulk fluid filtration, provides for bulk fluid entry beneficially from a direction countercurrent to filtration flow through the filtration medium, yet prevents the bulk fluid from encountering the downstream surface of the filtration medium; and provides for bulk fluid flow over upstream surface 20 of the filtration medium, cross-flow filtration through the filtration medium, and filtrate collection from the downstream side. Such a configuration may reduce air entrapment on the bulk fluid side of the filtration medium.

A suitable housing configuration of this type in accordance with the present invention, is illustrated in the drawing as containing a planar filtration medium, and is now described in the context of bulk fluid flow as depicted in FIG. 1. With reference to FIG. 2, a bulk fluid enters preferred apparatus 10 through an inlet port 30 in housing member 18 and is spread laterally from the conveniently centrally located, inlet port to ends 32,34 of a distribution groove 36 formed in member 18. The distribution groove or manifold is spaced apart from filtration medium 12 by a wall portion 38 of housing member 18 so as to prevent the entering bulk fluid from encountering the filtration medium. Fluid flow into manifold 36 is advantageously from a direction countercurrent to flow through filtration medium 12 (depicted in FIG. 3), and circumvents the filtration medium until fluid contact with upstream surface 20 of the filtration medium occurs.

Housing member 16 has recessed areas 40 for channeling fluid flow, separated by ribs 42 for bearing upon upstream surface 20 of the filtration medium. Ends 44 of channels 40 overlie and are in fluid communication with distribution manifold 36, and fluid exit ends 46 of channels 40 likewise overlie and are in fluid communication with a collection groove 48 formed in member 18. The collection groove or manifold is spaced apart from filtration medium 12 by a wall portion 50 of housing member 18 and is located at a side 52 of member 18 opposite distribution manifold 36.

The filtration medium has edges beneficially conventionally sealed to housing member 18, and overlies a filtrate collection well 54 formed in housing member 18. Collection well 54 is formed by channels 56, which are separated by filtration medium-supporting ribs 58 of housing member 18, and which lead to an outlet port 70. Filtrate passes through filtration medium 12, is collected in the filtrate collection channels, and directed to port 70. The portion of the bulk fluid that does not pass through the filtration medium, passes along upstream surface 20 of the filtration medium, is collected in groove 48, and exits filtration apparatus 10 through an outlet port 60, which is conveniently centrally located in the collection groove.

Filtrate collection channels 56 are in fluid communication with, and feed, a chamber 72 via port 70. Beneficially, port 70 is a channel having a narrow or flow-constricting cross-section so as to cause the filtrate to exit therefrom in drops, and chamber 72 has a filtrate inlet or mouth 74 of comparatively larger cross-section, and has a filtrate exit 76 of relatively smaller cross-section than mouth 74, at an output end 78. Typically, the filtrate exit has a larger cross-section than that of port 70, but in any event, exit 76 is sized to impede throughput so as to keep a liquid layer or body of filtrate, indicated by L, at output end 78. If desired, channel 70 could have a lip or extension at its fluid exit end.

Chamber 72, which is advantageously disposed proximate to filtration medium 12, can thus be understood to have a shape that generally decreases in cross-sectional area in the downstream direction. Such a shape is illustrated in FIG. 2 as being gradually tapered or generally conically-shaped, more precisely frustoconically-shaped, and beneficially directs drop flow to filtrate exit 76 of the chamber.

As explained earlier, an object of the present invention is to prevent bulk fluid contamination, and to this end, the present invention provides in one aspect, for an air gap downstream of the filtration medium. As a result of the air gap, filtrate that has entered chamber 72, is maintained spaced apart from the filtration medium.

As will become understood, drip-forming channel 70 and the configuration of chamber 72 provide, in use, for an air gap, indicated by G, to be formed within, and advantageously maintained within, chamber 72. Moreover, the greater cross-sectional area of mouth 74 of the chamber vis-a-vis that of drip-forming port 70 and that of filtrate exit 76, provides an independent contamination-preventing, safety effect. Proper function of the air gap is provided for by orienting drip port 70 and chamber 72 in the direction of gravity so that, within the chamber, there is a gas above a liquid layer.

Referring again to FIG. 1, a clamp or closed valve 8 in place at a suitable location 9 of conduit 6, beneficially forms a closed loop downstream of the filtration medium. As a result, before filtration begins, air on the filtrate side of the filtration medium occupies an initial volume provided by the space downstream of the filtration medium. As illustrated in the drawing, this space is defined in part by member 8 and is provided by drip-forming channel 70, chamber 72 and conduit 6. Moreover, the air occupying this space will be at an initial pressure which before filtration begins, will conveniently be atmospheric pressure but may be greater than atmospheric pressure if desired.

With continued reference to FIG. 2, when flow into filtration apparatus 10 is commenced, filtrate enters drip chamber 72 in drop form, exits chamber 72 through outlet 76, and flows down conduit 6 until it reaches member 8. Filtrate fills conduit 6 and then begins to fill the drip chamber.

The filtrate displaces air in conduit 6, but the air is trapped on the downstream side of the filtration medium by fluid pressure on the upstream side of the filtration medium and as a result, the trapped air occupies the drip chamber. Accordingly, an air gap is formed that separates filtrate downstream of the air gap from the filtration medium.

In this condition, there is a compression of the air volume and the air is consequently under an increased pressure. In accordance with an advantageous feature of the invention, the air head space reaches an increased pressure equal to the pressure on filtration medium surface 20; and at such time, filtration stops for the reason that no net force in the cross-flow direction exists, and the air occupies a smaller volume. During the period of time when filtration has stopped, there will beneficially be due to the air gap, no exchange between filtrate in chamber 72 and fluid on filtration medium surface 20 resulting from, for instance, osmotic or concentration gradients.

In the manner described, an air gap having a certain head pressure may be formed within chamber 72 and filtration automatically ceases. Thereafter, a process in accordance with the present invention, may be used for sampling, for instance, a bulk fluid, upon demand.

In one such approach, at a time when analysis is appropriate, valve 8 is opened to deliver filtrate previously collected, to waste line 5. As filtrate flows from conduit 6, the air expands and its pressure becomes less than the pressure on filtration medium surface 20, and filtration resumes. Thereafter, fresh filtrate is collected, and valve 8 may be opened to deliver fresh filtrate to analytical device 4. Then, valve 8 may be closed, as a result of which filtration will continue until the equilibrium pressure is again reached. Thereafter, this sequence may be repeated as and when necessary. In this way, a contamination-preventing, air gap may be formed and maintained within chamber 72, and the bulk fluid may be sampled upon demand, for filtrate analysis.

For sake of illustration, the drip-forming channel could have a diameter of about 0.1 cm; and chamber 72 could have a diameter of about 2 cm at mouth 74, and a diameter of about 0.15 cm at filtrate exit 76. It will be understood that a suitable chamber volume depends in part on the pressure to be provided on the upstream side of the filtration medium, and in regard thereto, for a volumetric size of about 4 ml, an air gap having a height of about 2.4 cm could be provided at a pressure of about 500 mm Hg above atmospheric pressure.

As can be understood, the provision of an air gap between the filtration medium and the filtrate in chamber 72 may advantageously prevent microbial contamination of a bulk fluid. For instance, deleterious microbes could move in an upstream direction through filtrate, and the air gap could prevent microbe entry into port 70 and eventual contact with filtration medium and bulk fluid. It will be of course understood, that situations may arise where the safety measures provided by this invention, are insufficient to prevent bulk fluid contamination.

A further benefit of the present invention is that self-cleaning of the upstream side of the filtration medium surface, is provided for. More precisely, a selfcleaning effect occurs between the collection of samples when there is a closed loop downstream of the filtration medium. In this condition, the only net force acting on the filtration medium is exerted across upstream surface 20, which force has a sweeping effect. As a result, in the case of plasmapheresis, accumulated protein is removed from surface 20, therefore restoring the filtering properties of the filtration medium for the next sample. This benefit may be realized in conjunction with sampling a bulk fluid upon demand.

Figure 3:
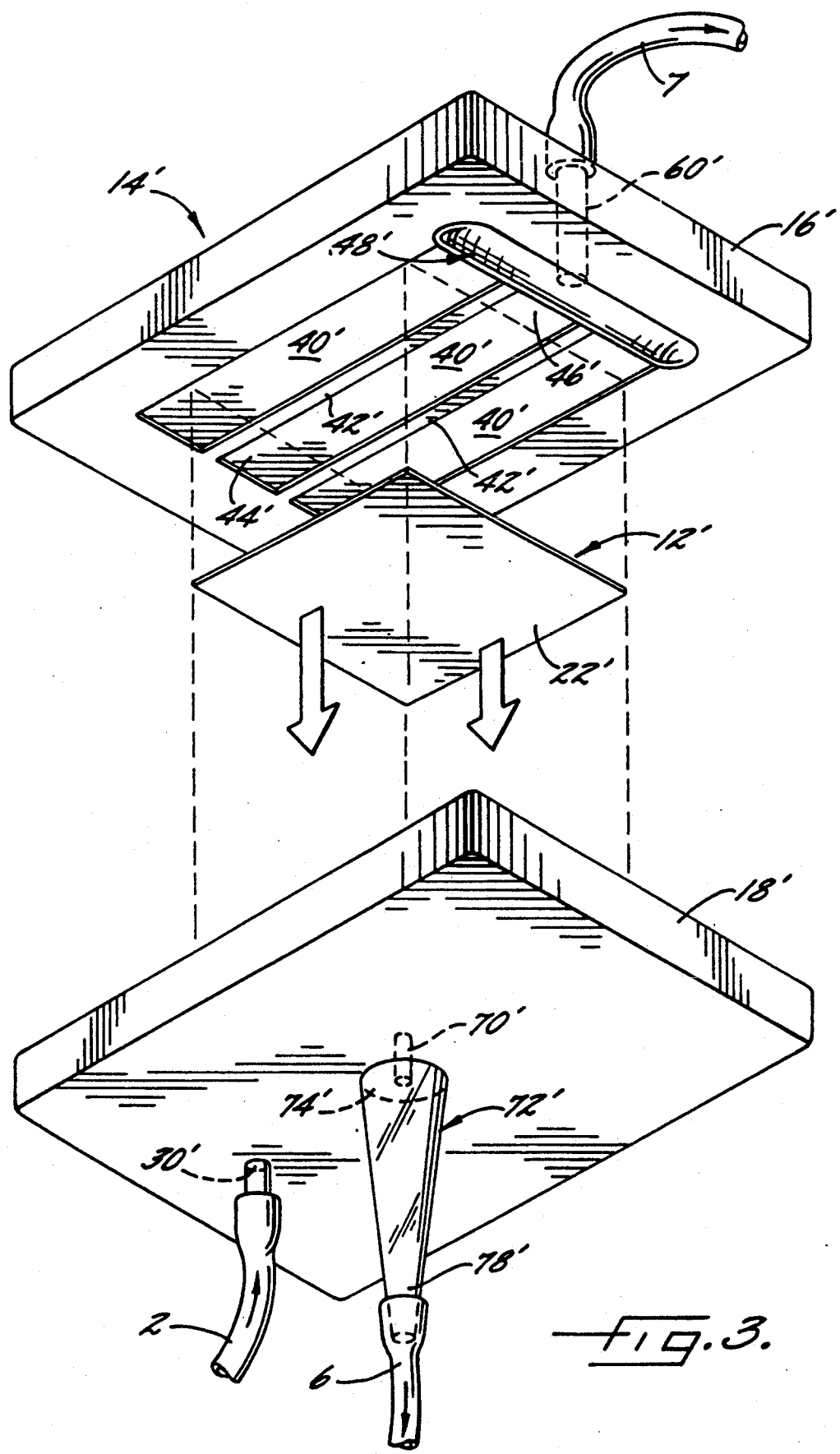
FIG. 3 is an exploded view of another embodiment of the filtration apparatus depicted in FIG. 1.

FIG. 3 shows a further preferred embodiment of the present invention, and differs from the embodiment of FIG. 2 with respect to the location of collection manifold 48', which is formed as a groove in housing member 16', and the location of fluid exit port 60', which is also formed in housing member 16'. Channels 40' flow directly into manifold 48'. Like parts have been indicated with like numbers.

By the invention described, a bulk fluid may be sampled for analysis, upon demand, and contamination thereof prevented. Furthermore, the upstream side of the filtration medium surface employed therein, can be cleaned between drawing samples, so as to restore the filtering properties.

Having described the invention in detail and by reference to preferred embodiments thereof, it will be apparent that modifications and variations are possible without departing from the scope of the invention defined in the appended claims. Several variants or modifications have been briefly mentioned for purposes of illustration.

I claim:

1. Filtration apparatus comprising a filtration medium disposed within a housing having fluid inlet means; a fluid flow path on an upstream side of said filtration medium and in fluid communication with said fluid inlet means; means for collecting unfiltered fluid from said upstream side of said filtration medium and in fluid communication with said fluid flow path; and means for preventing backflow-caused contact between a filtrate and said filtration medium by provision of an air gap downstream of said filtration medium, said contact-preventing means comprising a chamber in fluid communication with, and on a downstream side of, said filtration medium via a drip-forming channel, said chamber having a mouth of greater cross-section than a cross-section of said drip-forming channel, and having a filtrate exit of smaller cross-section than said mouth.

2. A filtration process for collection of a filtrate from a bulk fluid, said process comprising passing a bulk fluid to be filtered, into a filtration apparatus containing a filtration medium, wherein said fluid enters said filtration apparatus from a direction countercurrent to filtrate flow through said filtration medium; thereafter, without said fluid having contacted a downstream surface of said filtration medium, passing said fluid over an upstream surface of said filtration medium and effecting filtration of said fluid in a cross-flow direction to provide a filtrate, and collecting unfiltered fluid from an upstream side of said filtration medium; directing said filtrate toward a drip-forming channel disposed downstream of said filtration medium, passing said filtrate through said drip-forming channel and thereafter collecting said filtrate, and preventing contamination of fluid on said upstream surface by any contaminants downstream of said filtration medium, by forming an air gap between said filtrate and said filtration medium.

3. A filtration process for collection of a filtrate from a bulk fluid upon demand, said process comprising passing a bulk fluid to be filtered, into a filtration apparatus containing a filtration medium; passing said fluid over an upstream surface of said filtration medium and effecting filtration of said fluid in a cross-flow direction to provide a filtrate, and collecting unfiltered fluid from an upstream side of said filtration medium; directing said filtrate toward a drip-forming channel disposed downstream of said filtration medium, passing said filtrate through said drip-forming channel and thereafter collecting said filtrate, and forming an air gap between said filtrate and said filtration medium; thereafter forming a closed path downstream of said filtration medium, whereby said filtration ceases, the only net force acting on said upstream surface is exerted by said bulk fluid flowing over said upstream surface, and said air gap prevents, until said filtration resumes, contamination of said bulk fluid on said upstream surface by any contaminants downstream of said filtration medium; and thereafter opening said closed path to remove filtrate, whereby said filtration resumes and fresh filtrate is collected upon demand.

4. A filtration process for collection of a filtrate from a bulk fluid, said process comprising passing a bulk fluid to be filtered, into a filtration apparatus containing a filtration medium; thereafter, passing said bulk fluid over an upstream surface of said filtration medium and effecting filtration of said bulk fluid in a cross-flow direction to provide a filtrate, and collecting unfiltered fluid from an upstream side of said filtration medium; directing said filtrate toward a drip-forming channel disposed downstream of said filtration medium, passing said filtrate through said drip-forming channel and thereafter collecting said filtrate, and preventing contamination of fluid on said upstream surface by any contaminants downstream of said filtration medium, by forming an air gap between said filtrate and said filtration medium.

5. A filtration process for collection of a filtrate from a bulk fluid, said process comprising passing said bulk fluid into a filtration apparatus containing a filtration medium, wherein said bulk fluid enters said filtration apparatus from a direction countercurrent to filtrate flow through said filtration medium; thereafter, without said bulk fluid having contacted a downstream surface of said filtration medium, passing said bulk fluid over an upstream surface of said filtration medium and effecting filtration of said bulk fluid in a cross-flow direction to provide a filtrate, and collecting unfiltered fluid from an upstream side of said filtration medium and passing said unfiltered fluid from said filtration apparatus in said direction countercurrent to filtrate flow; directing said filtrate toward a drip-forming channel disposed downstream of said filtration medium, passing said filtrate through said drip-forming channel and thereafter collecting said filtrate, and preventing contamination of fluid on said upstream surface by any contaminants downstream of said filtration medium, by forming an air gap between said filtrate and said filtration medium.

6. The apparatus of claim 1, wherein said filtration medium has a microporous structure.

7. The apparatus of claim 1, wherein said filtration medium is planar.

8. The process of claim 2, wherein said bulk fluid is blood.

9. The process of claim 3, wherein said bulk fluid is blood.

10. The process of claim 4, wherein said bulk fluid is blood.

11. The process of claim 5, wherein said bulk fluid is blood.

* * * * *